United States Patent [19]

Boyle et al.

[11] Patent Number: 4,933,357

[45] Date of Patent: Jun. 12, 1990

[54] 1,3-DIAZOLYL-2-PHENYLALKYL-2-PROPANOL DERIVATIVES

[75] Inventors: Francis T. Boyle, Congleton; James M. Wardleworth, Macclesfield, both of England

[73] Assignee: Imperial Chemical Industries plc, London, England

[21] Appl. No.: 58,118

[22] Filed: Jun. 4, 1987

[30] Foreign Application Priority Data

Jun. 17, 1986 [GB] United Kingdom ............... 8614712

[51] Int. Cl.⁵ ..................... A61K 31/41; C07D 249/08
[52] U.S. Cl. .................................. 514/383; 548/266.6
[58] Field of Search ...................... 548/262; 514/383

[56] References Cited

U.S. PATENT DOCUMENTS

| | | | |
|---|---|---|---|
| 4,416,682 | 0/1983 | Worthington | 71/76 |
| 4,483,863 | 11/1984 | Richardson et al. | 548/262 |
| 4,602,025 | 7/1986 | Hirsch et al. | 548/262 |
| 4,609,666 | 9/1986 | Hirsch et al. | 548/262 |
| 4,625,036 | 11/1986 | Boyle | 548/262 |

FOREIGN PATENT DOCUMENTS 564060 4/1984 Australia .
165783 of 1985 European Pat. Off. .

*Primary Examiner*—Glennon H. Hollrah
*Assistant Examiner*—Patricia L. Morris
*Attorney, Agent, or Firm*—Cushman, Darby & Cushman

[57] ABSTRACT

Heterocyclic compounds of the formula:

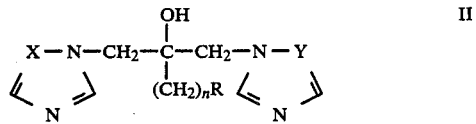

wherein X and Y, which may be the same or different, are each a $=N-$ or $=CH-$ group and R is a phenyl radical which optionally bears one or more substituents selected from halogen atoms, amino, cyano, carbamoyl, hydroxy and nitro radicals, 1–6C alkyl, halogenoalkyl, alkoxy, halogenoalkoxy and alkylamino radicals, di(-1–6C alkyl)amino and 2–6C alkoxycarbonyl radicals, and n is 1 to 6, but excluding the compound wherein X and Y are each $=N-$, R is 2,4-dichlorophenyl and n is 1; and the pharmaceutically or veterinarily acceptable acid addition salts thereof; processes for their manufacture; and pharmaceutical and veterinary compositions containing them.

1 Claim, No Drawings

1,3-DIAZOLYL-2-PHENYLALKYL-2-PROPANOL DERIVATIVES

This invention relates to triazole and imidazole compounds which are useful as aromatase inhibitors.

Aromatase is an enzyme which effects aromatisation of ring A in the metabolic formation of various steroid hormones. Various cancers, for example breast cancer, are dependent upon circulating steroid hormones which have an aromatic ring A. Such cancers can be treated by removing the source of ring A aromatised steroid hormones, for example by the combination of oophorectomy and adrenalectomy. An alternative way of obtaining the same effect is by administering a chemical compound which inhibits the aromatisation of the steroid ring A, and the compounds of the invention are useful for this purpose.

European Patent No. 44605 discloses a class of triazole and imidazole compounds of the formula I wherein $R^1$ is an optionally substituted alkyl, cycloalkyl, aryl or aralkyl radical, and $Y^1$ and $Y^2$ are =CH— or =N—. There is only disclosed, however, one characterised Example of a compound in which $R^1$ is an aralkyl radical, namely that in which $R^1$ is 2,4-dichlorobenzyl and $Y^1$ and $Y^2$ are each =N—. We have now found that compounds of the formula I wherein $R^1$ is an optionally substituted benzyl radical are very effective aromatase inhibitors.

Thus, according to the invention, there is provided a heterocyclic compound of the formula II wherein X and Y, which may be the same or different, are each a =N— or =CH— group and R is a phenyl radical which optionally bears one or more substituents selected from halogen atoms, amino, cyano, carbamoyl, hydroxy and nitro radicals, 1-6C alkyl, halogenoalkyl, alkoxy, halogenoalkoxy and alkylamino radicals, di(-1-6C alkyl)amino and 2-6C alkoxycarbonl radicals, and n is 1 to 6, but excluding the compound wherein X and Y are each =N—, R is 2,4-dichlorophenyl and n is 1; and the pharmaceutically or veterinarily acceptable acid addition salts thereof.

A suitable value for a halogen substituent in R is, for example, a fluorine, chlorine. bromine or iodine atom, and preferably a fluorine or chlorine atom. Preferred halogen-substituted phenyl values for R are therefore 2-, 3- and 4-fluorophenyl, 2-, 3- and 4-chlorophenyl, 2,3-, 2,4-, 2,5-, 2,6-, 3,4- and 3,5-difluorophenyl, 2,3-, 2,4-, 2,5-, 2,6-, 3,4- and 3,5-dichlorophenyl, and phenyl bearing mixed halogen substituents, for example 2-chloro-4-fluorophenyl and 4-chloro-2-fluorophenyl.

A suitable value for 1-6C alkyl substituent in R is, for example, a methyl, ethyl, propyl, isopropyl, butyl, isobutyl, sec-butyl, tert-butyl, pentyl or hexyl radical.

A suitable value for a 1-6C halogenoalkyl substituent in R is, for example. a trichloromethyl, fluoromethyl, difluoromethyl, trifluoromethyl, 1- or 2-chloroethyl, 2,2,2-trichloroethyl, 1- or 2-fluoroethyl, 1,1-, 1,2- or 2,2-difluoroethyl, 1,1,2-, 1,2,2- or 2,2,2-trifluoroethyl or 2,2,3,3,3-pentafluoropropyl radical.

A suitable value for a 1-6C alkoxy substituent in R is, for example, a methoxy, ethoxy, propoxy. isopropoxy, butoxy, isobutoxy, sec-butoxy, tert-butoxy, pentyloxy or hexyloxy radical.

A suitable value for a 1-6C halogenoalkoxy substituent in R is, for example. a fluoromethoxy, trifluoromethoxy, 2,2,2-trichloroethoxy, 1,1-, 1,2- or 2,2-difluoroethoxy, pentafluoroethoxy or 2,2,3,3,3-pentafluoropropoxy radical.

A suitable value for a 1-6C alkylamino substituent in R is, for example, a methylamino, ethylamino, propylamino, isopropylamino, butylamino, isobutylamino, sec-butylamino, tert-butylamino, pentylamino or hexylamino radical, and a suitable value for a di(1-6C alkyl)amino substituent is, for example, a dimethylamino, ethylmethylamino, diethylamino, methylpropylamino, ethylpropylamino, dipropylamino, dibutylamino, methylhexylamino or dihexylamino radical.

A suitable value for a 2-6C alkoxycarbonyl substituent in R is, for example, a methoxycarbonyl, ethoxycarbonyl, propoxycarbonyl, isopropoxycarbonyl, butoxycarbonyl or pentyloxycarbonyl radical.

Suitable pharmaceutically acceptable acid addition salts are, for example, hydrochlorides, hydrobromides, sulphates, nitrates, phosphates and toluene-p-sulphonates.

A preferred value for n is 1.

A preferred group of compounds of the invention comprises those compounds of the formula II wherein R bears at least one halogen substituent.

Preferred compounds of the formula II are 2-(4-chlorophenyl)-1,1-di(1,2,4-triazol-1-ylmethyl)ethanol, 2-(4-fluorophenyl)-1,1-di(1,2,4-triazol-1-ylmethyl)ethanol and 2-(2-fluoro-4-trifluoromethylphenyl)-1,1-di(1,2,4-triazol-1-ylmethyl)ethanol.

The compounds of the formula II may be prepared by processes known in themselves for the manufacture of chemically analogous compounds. Thus, according to a further feature of the invention there is provided a process for the manufacture of a compound of the formula II which comprises:

(a) the reaction of an epoxide of the formula III or IV, either as such, or formed in situ, with a heterocyclic compound of the formula V or VI respectively, or with an alkali metal salt thereof; or (b) the reaction of a halogeno compound of the formula VII, VIII, IX or X, wherein Z is a halogen, with a heterocyclic compound of the formula V or VI, or with an alkali metal salt thereof; or (c) the reaction of a ketone of the formula XI or XII with a Wittig reagent of the formula XIII or XIV respectively, wherein Q is a triphenylphosphine halide $(Z^-.Ph_3P^+-)$ or a dialkyl phosphono $[(R^2O)_2PO—]$ radical, wherein $R^2$ is a 1-6C lower alkyl radical, which Wittig reagent may be preformed or formed in situ, or with an organometallic reagent of the formula XV or XVI; wherein Q' is lithium or a group of the formula —MgZ.

(d) the reaction of an aralkyl ester of the formula XVII, wherein $R^2$ has the meaning stated above, with an organometallic reagent of the formula XV or XVI as defined above; whereafter if desired (i) a compound of the invention in which R bears a cyano substituent is hydrolysed with an acid to form a compound of the invention wherein R bears a corresponding carbamoyl substituent: or (ii) a compound of the invention in which R bears an alkoxycarbonyl substituent is reacted with ammonia to form a compound of the invention in which R bears a corresponding carbamoyl substituent; or (iii) a compound of the invention in which R bears a carbamoyl substituent is dehydrated with an acid anhydride to form a compound of the invention in which R bears a corresponding cyano substituent; or (iv) a compound of the invention in which R bears a nitro substituent is reduced to form a compound of the invention in which R bears a corresponding amino substituent; or (v) a compound of the invention in which R bears an amino substituent is alkylated to form a compound of the invention in which R bears a corresponding 1–6C alkylamino or di(1–6C)alkyl)-amino substituent; or (vi) a compound of the invention is nitrated to form a corresponding compound of the invention in which R bears a nitro substituent;

The epoxide of the formula III, wherein Y is =N—, used as starting material in the above process, may be obtained by bromination of a ketone of the formula $R(CH_2)_nCOCH_3$, with sodium bromite, or by reaction of a diazoketone compound, $R(CH_2)_nCOCH_2N_2$, with hydrogen bromide, to give an alpha-bromoketone $R(CH_2)_nCOCH_2Br$. This bromoketone is then reacted with a heterocyclic compound of the formula VI to form a heterocyclic compound of the formula XI, which is then reacted with dimethyl sulphonium methylide or dimethyl oxosulphonium methylide to form the required epoxide III.

Alternatively, the epoxide of the formula III may be obtained by epoxidising an olefin of the formula $R(CH_2)_nCH:CH_2$ (XVIII), for example with a peroxycarboxylic acid, to an epoxide XIX, which is then opened with a heterocyclic compound VI to form a hydroxy compound XX. The alcohol XX is then oxidised to the corresponding ketone X for example with chromic oxide (Jones' reagent), and the ketone is then reacted with dimethyl sulphonium methylide or dimethyl oxosulphonium methylide, to form the required epoxide III.

The epoxide IV, used as starting material in the above process, may be obtained similarly, using either of the two reaction sequences described above, but using the heterocyclic compound of the formula V instead of that of the formula VI.

The halogeno compound of the formula VII may be obtained by reacting a 1,3-dihalogenoacetone with the appropriate Grignard reagent, according to known methods (e.g. Johnson et al, J. Org. Chem, 1962, 27, 2241-3). The halogeno compound so obtained usually contains a minor proportion of the epoxide VIII, and it can readily be converted completely to the epoxide VIII, if so desired, by treatment with a base, such as sodium bicarbonate.

The halogeno compound of the formula IX, used as starting material in the above process, may be obtained by reacting a ketone of the formula XII with a Wittig reagent of the formula $CH_3Q$ to form an olefin of the formula XXI which is then reacted with a hypohalous acid in conventional manner.

Alternatively, the ketone XII may be reacted with dimethyl sulphonium methylide or dimethyl oxosulphonium methylide to form the epoxide IV, which is then opened with a hydrogen halide, HZ, for example hydrogen bromide; or the epoxide IV may be obtained by the peroxycarboxylic acid epoxidation of the olefin XXII.

The halogeno compound of the formula X, used as the starting material in the above process, may be obtained similarly, starting from the corresponding heterocyclic ketone XI.

The Wittig reagents of the formulae XIII and XIV, used as starting materials in the above process, may be manufactured by reacting 1-chloromethyl-1,2,4-triazole or 1-chloromethylimidazole with either triphenylphosphine, as described in European Patent Publication No. 60222, or with potassium diethyl phosphite.

According to a further feature of the invention there is provided a pharmaceutical or veterinary composition which comprises a pharmacologically effective amount of a compound of the formula I together with a pharmaceutically or veterinarily acceptable diluent or carrier.

The composition of the invention may be in a conventional pharmaceutical form suitable for oral or parenteral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 1 to 100, preferably 5 to 50 mg. of a compound of the invention.

According to a further feature of the invention there is provided the use of a heterocyclic compound of the formula II wherein X and Y, which may be the same or different, are each a =N— or =CH— group and R is a phenyl radical which optionally bears one or more substituents selected from halogen atoms, amino, cyano, carboxamido and nitro radicals, 1–6C alkyl, halogeno alkyl, alkoxy, halogenoalkoxy and alkylamino radicals, di(1–6C alkyl)amino and 2–6C alkoxycarbonyl radicals, and n is 1 to 6, for the manufacture of a pharmaceutical or veterinary composition having aromatase inhibitory activity.

Preferred values for R and n are those defined above, and specific preferred compounds of the formula II for use in this aspect of the invention are 2-(2,4-dichlorophenyl)-1,1-di(1,2,4-triazol-1-ylmethyl)ethanol, 2-(4-chlorophenyl)-1,1-di(1,2,4-triazol-1-ylmethyl)-ethanol and 2-(4-fluorophenyl)-1,1-di(1,2,4-triazol-1-ylmethyl)ethanol.

As indicated above, the compounds of the invention of the formula II, and the compounds employed in the use aspect of the invention, are useful as aromatase inhibitors. Aromatase inhibition may be demonstrated by the following tests:

DEMONSTRATION OF ACTIVITY IN VITRO

Aromatase inhibitory activity was measured using the enzyme present in the microsomal fraction of human term placenta, as described by Ryan, J. Biol, Chem. 234,268,1959. Enzyme activity was determined by measuring the amount of tritiated water released from 0.5 micromolar (1B,2B-$^3$H)testosterone after 20 minutes incubation at 37°. The method used was essentially that described by Thomson and Siiteri, J. Biol. Chem. 249,5364,1974 except that testosterone was used in place of androstenedione. Test compounds were dissolved in dimethylsulphoxide (DMSO) to achieve final concentrations of 2, 0.2 or 0.02ug/ml. The reaction was started by the addition of 50ul of microsome suspension to 50ul of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200ul of 5% (w/v) suspension of charcoal in 0.5% (w/v) solution of Dextran T70 in water. After 1 hour the charcoal was precipitated by centrifugation and 150ul of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4-day ovarian cycles are found to have ovulated at the time of the post-mortem examination. At an effective dose, aromatase inhibitors prevent ovulation i.e. no eggs are found in the fallopian tubes.

In the above test, the compounds of formula II are active at less than 1 ug/ml (in vitro) and less than 10 mg/kg (in vivo), and the preferred compounds of the formula I are active at below 0.1 ug/ml (in vitro) and 1.0 mg/kg (in vivo), and no indication of any toxicity has been seen at these doses.

The invention is illustrated, but not limited, by the following Examples, in which temperatures are given in degrees Celsius.

EXAMPLE 1

To a suspension of magnesium turnings (3.2 g.) in anhydrous diethyl ether (100 ml.) was added a solution of 4-chlorobenzyl chloride (16.1 g.) in anhydrous ether (200 ml.) at such a rate as to maintain gentle reflux. After keeping at reflux for a further 20 minutes the grey-green solution was cooled to −65° and a solution of 1,3-dichloroacetone (12.0 g.) in ether (100 ml.) was added dropwise over 20 minutes. Stirring was continued for 1 hr at −65°, then the solution allowed to warm to −25°, and a mixture of glacial acetic acid (15 ml.) in ether (100 ml.) was added, followed after 15 minutes by water (200 ml.). The organic layer was separated and the aqueous layer was extracted with ether. After washing the ether extracts with water and drying over sodium sulphate, evaporation gave a pale yellow oil (28.3 g).

The oil was dissolved in dry dimethylformamide (150 ml.) and sodium triazole (18.6 g.) was added in one portion. The black mixture was heated on the steam bath for 6 hours then cooled overnight. The mixture was poured into water (200 ml.) and extracted with ethyl acetate, the extracts were washed with brine, dried over sodium sulphate and the solvents were evaporated to give a black oil (28.7 g.). This was purified by column chromatography on silica using chloroform:methanol 9.5:0.5 v/v as eluent. The resulting yellow gum (3.89 g.) was crystallised slowly from ethyl acetate/hexane to give a low-melting polymorph of 2-(4-chlorophenyl)-1,1-di(1,2,4-triazol-1-ylmethyl)ethanol as an amorphous white solid (1.06 g.) with m.p. 116°–118°.

EXAMPLES 2–4

The process described in Example 1 was repeated, using the appropriately substituted benzyl chloride as starting material, to give:
2-phenyl-1,1-di(1,2,4-triazol-1-ylmethyl)ethanol, m.p. 130°–132° (Example 2).
2-(4-fluororphenyl)-1,1-di(1,2,4-triazol-lylmethyl) ethanol, m.p. 145°–147° (Example 3).
2-(2,4-difluorophenyl)-1,1-di(1,2,4-triazol-1-ylmethyl)ethanol, m.p. 129°–130° (Example 4).

EXAMPLES 5–6

The process described in Example 1 was repeated, using the appropriate Grignard reagents prepared from 4-chlorophenethyl bromide and 3-(4-chlorophenyl)propyl bromide to give respectively:
3-(4-chlorophenyl)-1,1-di(1,2,4-triazol-1-ylmethyl)-propanol, mp. 139°–140° (Example 5); and
4-(4-chlorophenyl)-1,1-di(1,2,4-triazol-1-ylmethyl)-butanol, hydrochloride salt mp 151°–154° (Example 6).

EXAMPLE 7

A mixture of 1-(4-chlorophenyl)-3-(1,2,4-triazol-1-yl)propan-2-one (15 g), trimethylsulphoxonium iodide (17.5 g), potassium hydroxide (8.57 g), 1,2,4-triazole (5.48 g) and tert-butanol (150 ml) was heated under reflux for 5 h, then cooled overnight. The excess tert butanol was evaporated under reduced pressure, and the residue was partitioned between ethyl acetate and water. The organic phase was separated, washed with water, dried, and evaporated to dryness to give a brown gum, which was purified by column chromatography on silica eluting with chloroform/methanol, 97:3 by volume, to give a high melting polymorph of 2-(4-chlorophenyl)-1,1-di(1,2,4-triazol-1-ylmethyl)ethanol, mp 170°.

The 1-(4-chlorophenyl) 3-(1,2,4-triazol-1-yl)propan-2-one used as starting material in the above process may be manufactured as follows:

To a suspension of magnesium turnings (9.6 g) in anhydrous ether (50 ml) was added dropwise a solution of p-chlorobromobenzene (76.6 g) in anhydrous ether (500 ml) at such a rate as to maintain reflux. After refluxing for a further 20 minutes, the solution was cooled to 5o and a solution of allyl bromide (48.4 g) in anhydrous ether (100 ml) was added over 15 minutes. After 30 minutes the solution was allowed to warm to room temperature, and then saturated ammonium chloride was added dropwise, cautiously to avoid excessive frothing. The organic layer was separated and the aqueous phase was extracted with ether. After washing the ether extracts with water and drying, evaporation of the solvent gave a pale yellow oil which was purified by fractional distillation to give 3-(4-chlorophenyl)prop-1-ene as a colourless oil, b.p. 72°–74°/4 mm Hg. (532 Pa).

To a solution of 3-(4-chlorophenyl)prop-1-ene (9.0 g) in chloroform (100 ml) was added portionwise metachloroperbenzoic acid (12.2 g), and the solution was stirred for 5 h at room temperature. The mixture was poured into water, the water layer was separated and the organic layer washed successively with sodium bicaronate, sodium sulphite and water. After drying, evaporation of the solvent gave 1-(4-chlorophenyl)-2,3-epoxypropane as a pale yellow oil. (9.51 g). NMR in $CDCl_3$:

2.49(1H,m), 2.75(1H,m), 2.8(2H,m), 3.1(1H,m), 7.24(4H,m).

To a suspension of potassium carbonate (8.14 g) and 1,2,4-triazole (8.14 g) in acetonitrile (100 ml) was added 1-(4-chlorophenyl)-2,3-epoxypropane (9.0 g), and the resulting suspension was heated to 70° for 4.5 h. The excess acetonitrile was evaporated under reduced pressure, and the residue was partitioned between ethyl acetate and water. The organic layer was separated, washed with water and dried, and the solvent was evaporated to give a colourless oil. Purification by column chromatography on silica, eluting with chloroform/methanol, 95:5 by volume, gave 1-(4-chlorophenyl)-3-(1,2,4-triazol-1-yl)-2-propanol as a colourless oil which crystallised on standing, m.p. 104°-6°.

To a solution of 1-(4-chlorophenyl)-3-(1,2,4-triazol-1-yl-2-propanol (10 g) in acetone (100 ml) was added Jones reagent (15 ml), and the solution was stirred for 30 minutes at room temperature. The mixture was diluted with ethyl acetate and basified with sodium bicarbonate solution. The ethyl acetate layer was filtered through kieselguhr ("Celite") and evaporated to dryness to give a white solid, which was triturated with ether to give the required 1-(4-chlorophenyl-3-(1,2,4-triazol-1-yl)propan-2-one as a semi-crystalline solid. m.p. 110°-111°.

EXAMPLES 8-15

The process described in Example 7 was repeated, using the appropriately-substituted-phenyl propan-2-one as starting material, and, where appropriate, imidazole in place of 1,2,4-triazole, to give the following compounds:

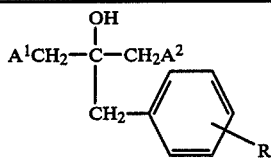

| Example | R | A¹ | A² | Mp. | Footnotes |
|---|---|---|---|---|---|
| 8 | 4-CH₃O | T* | T | 119-120 | 1,2 |
| 9 | 4-Cl | T | I* | (a) | |
| 10 | 2-F, 4-CF₃ | T | T | 170-171 | 1,3 |
| 11 | 4-CF₃ | T | T | 160-161 | 1,4 |
| 12 | 4-CF₃ | I | I | 177-178 | 1,5 |
| 13 | 4-CF₃ | T | I | 154-155 | 1,4 |
| 14 | 3-Cl | T | T | 112-114 | 1,6 |
| 15 | 4-CN | T | T | | |

*T = 1,2,4-triazol-1-yl, I = 1-imidazolyl.
(a) Nmr in deuteriochloroform: δ 2.61(2H,s), 4.0(4H,m), 5.4(1H,s), 6.88(1H,s), 7.22(1H,s), 7.3(4H,s), 7.6(1H,s), 8.02(1H,s), 8.35(1H,s).

Footnotes:
1. The propanone starting materials used in the manufacture of the above compounds were prepared by the sequence of reactions described in the latter part of Example 7, starting from the appropriate phenylpropene, and using imidazole in place of 1,2,4-triazole, as appropriate. The phenylpropenes were obtained from the reaction of the corresponding Grignard reagent with allyl bromide in conventional manner.
2. Via 1-(4-methoxyphenyl)-3-(1,2,4-triazolyl)-2-propanol. Nmr in d₆-dimethylsulphoxide: δ 2.65(2H,d), 3.73(3H,s), 4.15(3H,m), 4.95(1H,d), 7.0(4H,m), 7.9(1H,s), 8.4(1H,s); and 1-(4-methoxyphenyl)-3-(1,2,4-triazol-1-yl)propan-2-one. Nmr in deuteriochloroform: δ 3.7(5H,m), 5.05(2H,s), 7.0(4H,m), 7.98(1H,s), 8.05(1H,s).
3. Via 1-(2-fluoro-4-trifluoromethylphenyl)-3-(1,2,4-triazol-1-yl)-2-propanol. Nmr in deuteriochloroform: δ 8.0(1H,s), 7.8(1H,s), 7.2-7.6(3H,m), 4.37(1H,m), 4.2(2H,m), 3.46(1H,s), 2.9(2H,d); and 1-(2-fluoro-4-trifluoromethylphenyl) -3-(1,2,4-triazol-1-yl)propan-2-one, mp 93.5°-94.5°.
4. Via 3-(1,2,4-triazol-1-yl)-1-(4-trifluoromethylphenyl)-2-propanol, mp 90°-91°; and 3-(1,2,4-triazol-1-yl)-1-(4-trifluoromethylphenyl)propan-2-one, mp 99°-100°.
5. Via 3-(1-imidazolyl)-1-(4-trifluoromethylphenyl)-2-propanol, mp 98°-99°; and 3-(1-imidazolyl)-1-(4-trifluoromethylphenyl)propan-2-one, mp 128°-129°.
6. Via 1-(3-chlorophenyl)-3-(1,2,4-triazol-1-yl)-2-propanol. Nmr in deuteriochloroform: δ 2.7(2H,d), 4.1(3H,m), 7.1(4H,m), 7.7(1H,s), 7.9(1H,s), and 1-(3-chlorophenyl)-3-(1,2,4-triazol-1-yl)propan-2-one.

EXAMPLE 16

To a suspension of 3-(4-chlorophenylmethyl)-1,3-di(1,2,4-triazol-1-yl)propan-2-ol (0.5 g) in concentrated sulphuric acid (1 ml) was added dropwise mixed acid (comprising 0.015 ml nitric acid, d=1.42, and 0.5 ml concentrated sulphuric acid), and the suspension was stirred at room temperature for 36 h. The mixture was poured into ice water (50 ml) and basified with sodium bicarbonate before extraction with ethyl acetate. The organic layer was separated, washed with water, dried and evaporated to dryness to give a pale yellow solid, which was crystallised from ethyl acetate/hexane to yield 2-(4-chloro-3-nitrophenyl)-1,1-di(1,2,4-triazol-1-ylmethyl)ethanol, m.p. 136°-137°.

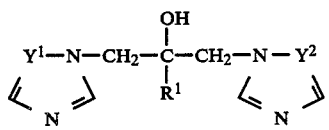

I

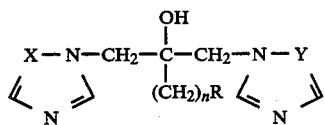

II

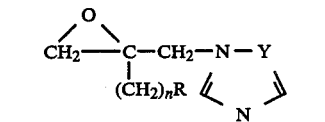

III

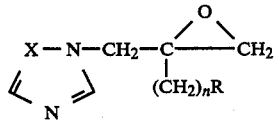

IV

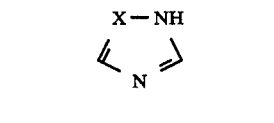

V

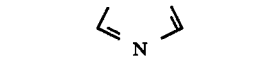

VI

-continued

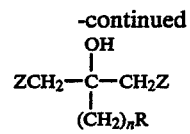

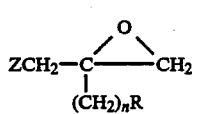

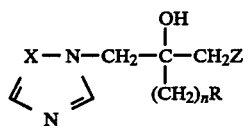

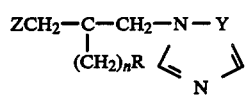

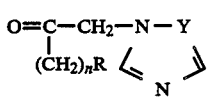

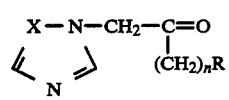

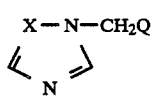

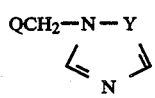

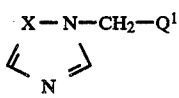

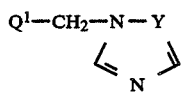

-continued

   VII

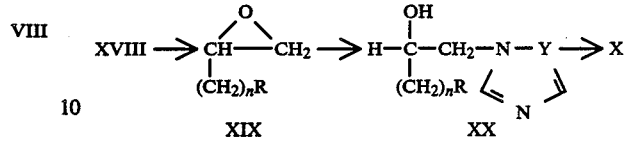   XVII / XVIII / VIII / XIX / XX

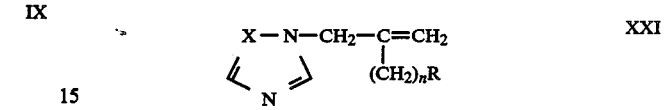   IX / XXI

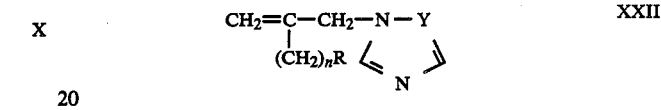   X / XXII

We claim:

1. A method of producing an aromatase inhibitory effect in a mammalian host in need of such treatment which comprises administering to said host an mount of a heterocyclic compound of the formula

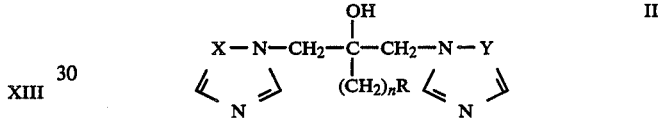   II wherein X and Y are each a =N— group and R is a phenyl radical which optionally bears one or more substituents selected from the group consisting of halogen atoms, amino, cyano, carbamoyl, hydroxy and nitro radicals, 1–6C alkyl, 1–6C halogenoalkyl, 1–6C alkoxy, 1–6C halogenoalkoxy and 1–6C alkylamino radicals di(1–6C alkyl)amino and 2–6C alkoxycarbonyl radicals, and n is 1 to 6, but excluding the compound wherein X and Y are each =N—, R is 2,4- or 2,6-dichlorophenyl and n is 1, or a pharmaceutically or veterinarily acceptable acid addition salt thereof, sufficient to produce said aromatase inhibitory effect.

* * * * *